United States Patent [19]

Sing

[11] 4,351,904

[45] Sep. 28, 1982

[54] BLEND OF NORMAL AND MUTANT STREPTOCOCCUS DIACETILACTIS

[76] Inventor: Edmond L. Sing, 3860 Cheviot Pl., Indianapolis, Ind. 46226

[21] Appl. No.: 281,915

[22] Filed: Jul. 9, 1981

Related U.S. Application Data

[60] Division of Ser. No. 137,243, Apr. 4, 1980, Pat. No. 4,319,928, which is a continuation-in-part of Ser. No. 105,102, Dec. 19, 1979, abandoned.

[51] Int. Cl.³ .................. C12N 1/20; A23C 19/06
[52] U.S. Cl. ........................... 435/253; 426/34; 426/38; 426/43; 426/61; 435/172; 435/260
[58] Field of Search .................. 426/34, 38, 42, 43, 426/61; 435/172, 253, 260

[56] References Cited

U.S. PATENT DOCUMENTS

| | | | |
|---|---|---|---|
| 3,968,256 | 7/1976 | Sing | 426/43 X |
| 4,172,899 | 10/1979 | Vedamuthu | 426/43 X |
| 4,191,782 | 3/1980 | Vedamuthu | 426/38 |
| 4,262,023 | 4/1981 | Eddy et al. | 426/43 X |

OTHER PUBLICATIONS

Burrow, et al., Characterization of Diacetyl Negative Mutants of *Streptococcus diacetilactis*, J. Da. Sci., vol. 53, No. 2, 1970, (pp. 121–125).

Kempler, et al., Applied and Environmental Microbiology, vol. 37, 1979, (pp. 316–323 and 1041–1043).

Webb, et al., By Products from Milk, 2nd Ed., The Ava. Publ. Co., Inc., Westport, Conn., 1970, (pp. 24–29).

*Primary Examiner*—David M. Naff
*Attorney, Agent, or Firm*—Woodard, Weikart, Emhardt & Naughton

[57] ABSTRACT

A bacteria-containing composition for use in making cottage cheese is prepared containing a strain of *Streptococcus diacetilactis* that produces substantial amounts of diacetyl in a milk culture, a strain of diacetyl deficient mutant *Streptococcus diacetilactis* that produces essentially no diacetyl in a milk culture and a suitable carrier for maintaining viability of the *Streptococcus diacetilactis*. By the use of the two types of *Streptococcus diacetilactis*, a manufacturer of cottage cheese can optimize both the cell count to achieve the desired inhibition of spoilage bacteria and flavor production to achieve the desired flavor in the finished product.

5 Claims, No Drawings

BLEND OF NORMAL AND MUTANT STREPTOCOCCUS DIACETILACTIS

This application is a division of application Ser. No. 137,243, filed Apr. 4, 1980, now U.S. Pat. No. 4,319,928, which is a continuation-in-part of application Ser. No. 105,102, filed Dec. 19, 1979, now abandoned.

BACKGROUND OF THE INVENTION

Much work has been done in the dairy industry relating to the production of aroma. Aroma production in milk was considered in 1933 by Michaelian, Farmer, and Hammer, *The Relationship of Acetylmethylcarbinol and Diacetyl to Butter Cultures*, Iowa Agr. Expt. Sta., Research Bull. 155. This article reports that citric acid-fermenting bacteria could produce large amounts of aroma compound diacetyl. In 1941, Hoecker and Hammer investigated the ability of *Streptococcus diacetilactis* to produce aroma in butter. *Flavor Development in Salted Butter by Pure Cultures of Bacteria*, Iowa Agr. Expt. Sta., Research Bull. 290 (1941).

By 1961 Lundstedt had developed a procedure for enhancing the flavor of cottage cheese and other dairy products through the use of *Streptococcus diacetilactis*. (U.S. Pat. No. 3,048,490). Moseley, Elliker and Sandine developed a variation on the Lundstedt process for making cottage cheese by 1964 (U.S. Pat. No. 3,323,921). In 1970, a still further variation of the process of making cottage cheese was developed by Sing (U.S. Pat. No. 3,968,256). This process involved the bulk addition of concentrated *Streptococcus diacetilactis* to cottage cheese without the need for further incubation. In all of these processes, one of the objects was to use *Streptococcus diacetilactis* because it produced diacetyl which enhanced the flavor.

It was also observed in the early 60's that the presence of *Streptococcus diacetilactis* had an inhibitory effect on spoilage organisms. In order to achieve the maximum inhibition of spoilage organisms, a relatively high concentration of *Streptococcus diacetilactis* in the finished cheese would be desired. However, if such a large concentration of *Streptococcus diacetilactis* were used, there was a tendency for excess production of the flavor compounds of diacetyl and acetaldehyde. Thus with the known processes of the prior art, one could obtain either an ideal maximum shelf life or an ideal flavor production, but not both. Efforts to overcome these problems lead to attempts to isolate strains of bacteria which had less flavor but which retained the full inhibitory effect.

In 1969, Burrow, Sandine, Elliker and Speckman pointed out the problem of too much flavor when maximum shelf life was obtained. *Characterization of Diacetyl Negative Mutants of Streptococcus diacetilactis*, Journal of Dairy Science, Vol. 53, p. 121-125. They noted that there was a need for strains of *S. diacetilactis* with impaired abilities to synthesize diacetyl. It was suggested in this 1969 article that since acetaldehyde appears to be a precursor of diacetyl during citrate metabolism, it was also believed that mutants of *S. diacetilactis* could be isolated with reduced aldehyde production. The authors reported that "Such strains would prove useful in manufacturing cultured products which often suffer from the green flavor defect." The authors reported that mutants of *Streptococcus diacetilactis* which they had developed produced an average of forty percent more lactic acid than parent strains; had acetaldehyde production which varied from quantities equal to the wild type to less than one-third the amount produced by the parents; and which retained inhibitory powers against food spoilage bacteria similar to their respective parents. However, the high acid and acetaldehyde production by the isolated mutants made their use in cottage cheese dressing impractical. The article suggested that this approach to extending the shelf life of cottage cheese and other foods seemed promising and reported that efforts were being continued to isolate new mutants which would produce less acid and aldehyde and still yield high cell numbers.

While efforts along this line had met with failure and research along this line had apparently ended, research concerning the biochemical pathways of *Streptococcus lactis* and *Streptococcus diacetilactis* has been taking place. In work of Kempler and McKay, studies of plasmid activity within *Streptococcus diacetilactis* led to the generation of various mutant forms of *Streptococcus diacetilactis*. Two articles about this work are entitled "Characterization of Plasmid Deoxyribonucleic Acid in *Streptococcus lactis* Subsp. diacetilactis: Evidence for Plasmid-Linked Citrate Utilization", *Applied and Environmental Microbiology*, Feb. 1979, pp. 316-323, Vol. 37, No. 2 and "Genetic Evidence for Plasmid-Linked Lactose Metabolism in *Streptococcus lactis* Subsp. diacetilactis", *Applied and Environmental Microbiology*, May, 1979, pp. 1041-1043, Vol. 37, No. 5. In studying the mechanism of the production of diacetyl from citrate as well as the lactose metabolism of *Streptococcus diacetilactis*, the authors Kempler and McKay treated *S. diacetilactis* strains 18-16 and DRC1 with acridine orange to eliminate various ones of the plasmids which were within the bacteria. As early as 1972, McKay et al. showed that acriflavin treatment of *S. diacetilactis* 18-16 resulted in the appearance of lactose-negative derivatives, implying the involvement of plasmid DNA in lactose utilization. While innumerable mutants were developed during the 70's for the purpose of determining the biological mechanisms of the bacteria, there were no reports of Kemper and McKay over the retention or lack of retention of inhibitory powers against food spoilage bacteria. Indeed, most of the mutant bacteria only had value in the research setting since they often had commercially desirable metabolic pathways significantly damaged by the mutating procedure. Thus the typical mutant developed for purposes of understanding the metabolic pathways was not considered as a bacterium which had commercial application. Most mutants of this type would be totally unsuited for commercial use.

SUMMARY OF THE INVENTION

The invention relates to a blend of a first type of *Streptococcus diacetilactis* containing both a normal acetaldehyde- and diacetyl-producing strain and a second mutant type which retains its ability to inhibit food spoilage bacteria but does not have an appreciable amount of diacetyl or acetaldehyde production when grown in a milk substrate. The blend is added to achieve in the final cheese a cell count of at least one million cells per gram of the finished cheese. Through the use of the two types of *S. diacetilactis*, for the first time, a manufacturer of cottage cheese can optimize both the cell count to achieve the desired inhibition and the flavor production to achieve the desired flavor in the finished product.

Applicant has discovered that two of the mutant strains used by Kempler and McKay not only produce little or no acetaldehyde or diacetyl, but also do not produce other undesirable products such as excess acid. Yet these mutant strains retain their inhibitory properties against spoilage organisms. While these strains have the defect of essentially no flavor production, this defect can be overcome with proper proportioning with a normal strain. For the first time, cottage cheese can be made with the maximum possible shelf life obtainable from *S. diacetilactis* and yet have virtually any amount of flavor that may be desired, from very mild to strong.

DESCRIPTION OF THE PREFERRED EMBODIMENT

In describing the invention, reference will be made to specific examples of the invention for purposes of illustration of the principles related to the invention and for purposes of disclosing the preferred method of practicing the invention in a manner which will enable a person of ordinary skill to practice the invention in its various forms.

In the preferred embodiment, a normal and a mutant strain are used. Reference to "normal strain" or "normal *Streptococcus diacetilactis*" as used herein is intended to include any strain of *Streptococcus diacetilactis* which will produce substantial amounts of diacetyl in a milk culture and which has the characteristic of inhibition of spoilage organisms which is typical of *Streptococcus diacetilactis*. Many of the normal strains of *Streptococcus diacetilactis* are known. The preferred strain is A.T.C.C. No. 15346 used by Sing in U.S. Pat. No. 3,968,256 and Moseley, Elliker and Sandine in U.S. Pat. No. 3,323,921.

Mutant strains which are suitable for use with the invention include strains 818 and 819, or their equivalent. These strains have been deposited in the Stock Culture Collection of the U.S. Department of Agriculture, Northern Regional Research Laboratory, Peoria, Ill. 61604, from which organization samples of these strains may be obtained. Strain 818 has been assigned the accession number of NRRL B-12070. Strain 819 has been assigned the accession number NRRL B-12071.

After selecting a normal and a mutant strain, the *Streptococcus diacetilactis* are separately grown in conventional fashion and thereafter the cells are separated from the growth media in the form of a paste as set forth in U.S. Pat. No. 3,968,256, which is incorporated herein by reference. From 5 to 95 parts of the cell paste normal strain are added to from 5 to 95 parts of the cell paste containing the mutant strain of 818 or 819 (or the equivalent). To this blend are added additional parts of a suitable carrier for maintenance of viability but not in sufficient amounts to dilute the total *Streptococcus diacetilactis* cell count to as low as $3 \times 10^9$ cells per gram.

The resultant bacteria-containing composition is then placed in small containers. These containers are sealed and cooled to below 0° C., typically below $-20°$ C., more preferably below $-30°$ C. With the preferred carrier, the contents become frozen at this low temperature.

While there is illustrated the preferred method of separately obtaining a paste for each of the two strains, it would be possible also to mix prior to obtaining the paste, either by growing the two strains together or by mixing the separate ripened cultures prior to separation of the cells. If the cells are grown to a sufficient concentration of cells above $3 \times 10^9$ cells per gram, the separation step can be eliminated. With this procedure, the suitable carrier could be incorporated as a part of the media.

When it is desired to make cottage cheese, a sealed container of the bacteria-containing composition is warmed to above 0° C. and preferably added to and mixed with a cottage cheese creaming mixture. The creaming mixture is then added to cottage cheese curds and blended in the conventional manner. The bacteria-containing composition is added in an amount to achieve at least $1.0 \times 10^6$ cells of *Streptococcus diacetilactis* per gram of cottage cheese.

EXAMPLE 1

Fifty liters of citrate-containing heat treated milk substate medium is cooled to about 30° C. and then inoculated with an active culture of *Streptococcus diacetilactis* A.T.C.C. No. 15346 in sufficient amount to provide a luxurious growth after about 12–16 hours. After the luxurious growth is obtained, the culture is then centrifuged to obtain a cell-containing paste which is separated from the supernatant. The harvested paste is diluted with a phosphate buffered diluent containing 2% monosodium glutamate to obtain an optimum pH of 6.6–6.8 for maintenance of viability and to standardize the preparation of this first strain to a known cell concentration of $1.5 \times 10^{11}$ cells per gram.

While the preparation of the first strain is progressing, 450 liters of heat treated milk substrate medium is cooled to about 30° C. and then inoculated with an active culture of *Streptococcus diacetilactis* strain 818 in sufficient amount to provide a luxurious growth after about 12–16 hours. After the luxurious growth is obtained, the culture is then centrifuged to obtain a cell-containing paste which is separated from the supernatant. The harvested paste is diluted with a phosphate buffered diluent containing 2% monosodium glutamate to obtain an optimum pH of 6.6–6.8 for maintenance of viability and to standardize the preparation of this second strain to a known concentration of $1.5 \times 10^{11}$ cells per gram.

Ninety parts of the standardized preparation of the second strain are added to and mixed with 10 parts of the standardized preparation of the first strain. This mixture is then placed in 60 gram, 240 gram and 400 gram containers which are sealed and cooled to $-40°$ C., more preferably to $-50°$ C., until the contents are frozen. These frozen containers are then shipped to dairy plants and stored at temperatures below $-20°$ C., more preferably to $-30°$ C. until needed.

At the dairy plants, cottage cheese curd is prepared in conventional fashion. Cottage cheese creaming mixture is also prepared in conventional fashion except that the frozen mixture is thawed, removed from its container and added to and mixed with the creaming mixture. The amount of frozen mixture used is sufficient to achieve a cell count of about 10 million cells per gram in the finished cottage cheese. (Roughly 30 grams of the mixture per 1000 lbs. of the cottage cheese). The creaming mixture is then blended with the curd in conventional fashion. The finished cottage cheese is kept cool to prevent significant growth of bacteria.

The cottage cheese produced has an excellent mild flavor and excellent shelf life.

A comparison is made to illustrate the advantages of this cottage cheese:

(1) Cottage cheese produced according to Example 1, with 10 parts of the first strain and 90 parts of the second strain.
  (a) flavor: desirable mild diacetyl flavor progressing to moderate after 30 days.
  (b) shelf life: about 40 days at 7.2° C.
(2) Cottage cheese produced having the same total cell count of *Streptococcus diacetilactis* as in Example 1 but only with the first strain of *Streptococcus diacetilactis*
  (a) flavor: strong diacetyl flavor progressing to very strong after 30 days
  (b) shelf life: about 40 days at 7.2° C.
(3) Cottage cheese produced having the same total cell count of *Streptococcus diacetilactis* but only with the second strain of *Streptococcus diacetilactis*
  (a) flavor: no diacetyl flavor
  (b) shelf life: about 40 days at 7.2° C.
(4) Cottage cheese produced having 10% of the total cell count of *Streptococcus diacetilactis* as in Example 1, but only with the first strain of *Streptococcus diacetilactis*
  (a) flavor: desirable mold diacetyl flavor progressing to moderate after about 20 days
  (b) shelf life: about 30 days at 7.2° C.
(5) Cottage cheese produced having 10% of the total cell count of *Streptococcus diacetilactis* as in Example 1, but only with the second strain of *Streptococcus diacetilactis*.
  (a) flavor: no diacetyl flavor
  (b) shelf life: about 30 days at 7.2° C.
(6) Cottage cheese produced without any *Streptococcus diacetilactis*.
  (a) flavor: no diacetyl flavor
  (b) shelf life: less than 20 days at 7.2° C.

EXAMPLE 2

The procedure of Example 1 is repeated except that a ratio of 50 parts of strain 1 and 50 parts of strain 2 is used. Similar results are achieved.

EXAMPLE 3

The procedure of Example 1 is repeated except that strain 819 is substituted for strain 818. Similar results are achieved.

EXAMPLE 4

The procedures of Examples 1 and 3 are repeated except that a ratio of 33 parts of strain 1 and 67 parts of strain 2 are used. Similar results are achieved.

What is claimed is:

1. A bacteria-containing composition which comprises:
  (a) from 5 to 95 parts of a first strain of *Streptococcus diacetilactis* that produces substantial amounts of diacetyl in a milk culture;
  (b) from 5 to 95 parts of a second strain of diacetyl deficient mutant *Streptococcus diacetilactis* selected from the group consisting of mutant strains NRRL B-12070 and NRRL B-12071 that produces essentially no diacetyl in a milk culture; and
  (c) additional parts of a suitable carrier for maintenance of viability, and
said composition having over $3 \times 10^9$ cells of *Streptococcus diacetilactis* per gram of said composition.

2. A packaged form of the composition of claim 1 which additionally includes a sealed container containing the composition of claim 1.

3. The packaged form of claim 2 in which the contents of said container are below 0° C.

4. The packaged form of claim 3 in which the contents of said container are frozen.

5. The packaged form of claim 3 in which the contents of said container are below −30° C.